United States Patent [19]

Mukogawa et al.

[11] Patent Number: 4,765,963

[45] Date of Patent: Aug. 23, 1988

[54] APPARATUS FOR MEASURING IMPURITIES IN WATER

[75] Inventors: Yasukazu Mukogawa; Katsuhiko Tamura; Takaaki Fukumoto, all of Itami, Japan

[73] Assignee: Mitsubishi Denki Kabushiki Kaisha, Tokyo, Japan

[21] Appl. No.: 911,354

[22] Filed: Sep. 24, 1986

[30] Foreign Application Priority Data

Sep. 24, 1985 [JP] Japan ................. 60-211572

[51] Int. Cl.[4] .............. G01N 31/02; G01N 33/18; G01N 35/08
[52] U.S. Cl. .................. 422/68; 422/101; 436/39; 436/52; 436/148; 73/61.4; 210/87
[58] Field of Search .............. 422/68, 93, 101; 73/61 R, 53, 61.4, 28, 63; 436/52, 53, 148, 39; 210/340, 341, 87

[56] References Cited

U.S. PATENT DOCUMENTS

| | | |
|---|---|---|
| 3,236,095 | 2/1966 | Gelder . |
| 3,452,586 | 7/1969 | Childs et al. . |
| 3,499,315 | 3/1970 | Marino . |
| 3,872,710 | 3/1975 | Louvel ................. 73/61.4 |
| 4,024,754 | 5/1977 | Alfthan ................. 73/63 |
| 4,117,715 | 10/1978 | Hoenig ................. 73/28 |
| 4,117,717 | 10/1978 | Isley . |
| 4,123,932 | 11/1978 | Baker et al. ........... 73/28 |
| 4,263,805 | 4/1981 | Isley et al. . |
| 4,361,028 | 11/1982 | Kamiya et al. ......... 73/28 |
| 4,446,726 | 5/1984 | Hockenberry ........... 73/61.4 |
| 4,513,607 | 4/1985 | Coupal ................. 73/61.4 |
| 4,521,864 | 6/1985 | Characklis . |
| 4,550,591 | 11/1985 | Cox et al. ............. 73/28 |
| 4,554,822 | 11/1985 | Eisenhauer et al. ..... 73/53 |

FOREIGN PATENT DOCUMENTS

| | | |
|---|---|---|
| 1726563 | 5/1956 | Fed. Rep. of Germany . |
| 1946505 | 7/1964 | Fed. Rep. of Germany . |
| 1598395 | 6/1971 | Fed. Rep. of Germany . |
| 2916036 | 6/1980 | Fed. Rep. of Germany . |
| 53-76891 | 7/1978 | Japan . |

OTHER PUBLICATIONS

"SDI Method", Handotai Process Zairyo Jitsumu Binran, p. 438, Published By Science Forum Company, Apr. 25, 1983.
Dr. F. Sierp, "Vom Wasser, 6, 1932," pp. 253–254.
Jens Muller et al., "Gwf Wasser/Abwasser, No. 5, 117 (1976)", p. 220.
Chem. Techn., 24 Jg. Heft 12, Dec. 1972, pp. 748–750.

Primary Examiner—Michael S. Marcus
Assistant Examiner—Jill Johnston
Attorney, Agent, or Firm—Lowe, Price, LeBlanc, Becker & Shur

[57] ABSTRACT

A sampled flow of water is extracted from a water conduit 1 carrying impure water by a sampling tube 2, the pressure at a point in the sampling tube is kept constant by a constant pressure maintaining valve 4, and the sampled water passed through a filter 7. The flow rate of sampled water passing through the filter 7 is measured by a flow meter 8. A value corresponding to the total amount or level of impurity in the sampled water is evaluated by an operation circuit 9 at a prescribed time interval, based on the time-dependent change in the result of measurement of the flow meter 8 and the total amount or level of impurities in pure water is thus measured indirectly.

2 Claims, 1 Drawing Sheet

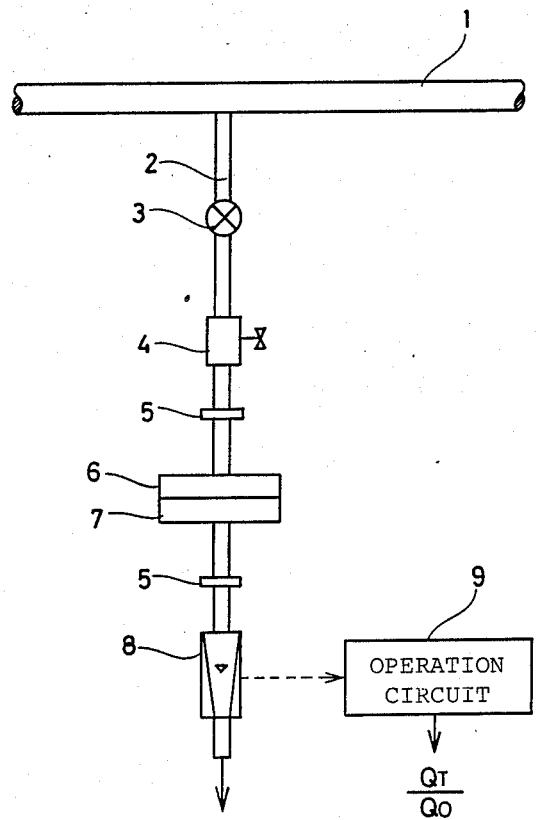

APPARATUS FOR MEASURING IMPURITIES IN WATER

BACKGROUND OF THE INVENTION

1. Field of the Invention

The present invention relates to a apparatus for measuring impurities in water, and more particularly to an apparatus for measuring the total amount or level of impurities in water based on the time-dependent change of flow rate of the water passed through a filter.

2. Description of the Prior Art

Conventionally, a direct microscopic method, the FI (Fourier Index) value method (disclosed as the SDI method in Handotai Process Zairyo Jitsumu Binran p. 438 published by Science Forum Company, Apr. 25, 1983, for example), and the like, have been known as methods for evaluating the purity of water. According to the first method, water extracted at an actual supply is filtered through a filter of 0.2 μm hole diameter and the minute particles on the filter are examined with a microscope. According to the second method, a prescribed amount of water is passed through a filter of 0.45 μm hole diameter under a constant pressure and the time for such passage is measured.

It is known that among impurities found in water there are materials of extremely small particle diameter, such as a colloidal material. However, in the above-described direct microscopic method, only minute particles larger than 0.2 μm can be captured, so that the above-described colloidal material can not be measured. In addition, much labor and skill are required in the measurement. In the FI value method, only filters having hole diameters larger than 0.45 μm are used at present in consideration of the time required for filtering. Therefore, only minute particles larger than 0.45 μm can be captured so that amounts of the aformentioned colloidal materials can not be measured.

In addition, neither of the above described methods is capable of continuous monitoring in the field, where water is used, and neither of them can cope with a sudden change in the quality of the water.

SUMMARY OF THE INVENTION

It is an object of the present invention to provide an apparatus, for measuring impurities in water, which is capable of measuring the total amount or level of impurities in water in an extremely simple and continuous manner in the field where water is used, and which is also capable of measuring impurities having small particle diameters.

Briefly stated, according to the present invention, the pressure of flowing impure water, i.e., water containing filterable impurities, passing through a sampling tube is kept constant and the flow is filtered through a filter. A value corresponding to the total amount or level of impurities in the impure water is evaluated based on the time dependent change in the flow rate passing through the filter.

If there are impurities in the water, they are captured on the filter and clog the holes of the filter, decreasing the flow rate of the water passing through the filter as time passes. In view of the above-described fact, the present invention is adapted to measure the total amount or level of impurities in water indirectly, by examining the time-dependent change in the constant pressure driven flow rate of water passing through the filter for a long time.

According to the present invention, the total amount or level of impurities in impure water can be measured in an extremely simple and continous manner, without any skill, in the field where the waater is used. Accordingly, a sudden change in the quality of water can be detected. In addition, even if the characteristic particle diameter of the impurities is small, the filter is clogged gradually as the sampled water passes through the filter for a long time, so that even in this case the measurement of impurity level can be carried out.

These objects and other objects, features, aspects and advantages of the present invention will become more apparent from the following detailed description of the present invention when taken in conjunction with the accompanying drawings.

BRIEF DESCRIPTION OF THE DRAWINGS

FIG. 1 is a schematic diagram showing a structure of the preferred embodiment of the present invention.

DESCRIPTION OF PREFERRED EMBODIMENTS

FIG. 1 is a schematic diagram showing a structure of the preferred embodiment of the present invention. In the figure, impure water which is actually used in the field is flowing through a water conduit 1. A sampling pipe 2 is coupled to water conduit 1. The sampling pipe 2 is to guide part of the water flowing in water conduit 1 to an impurity measuring apparatus. A manual valve 3 and a constant pressure.maintaining valve 4 are provided in sampling pipe 2. Valve 3 can be opened and closed manually. The constant pressure maintaining valve 4 holds the pressure constant, allowing a corresponding flow rate of the sampled water through sampling pipe 2.

A filter housing is coupled to the sampling pipe 2 by means of a pair of joints 5. This filter housing contains a filter holder 6 and a filter 7. The filter holder 6 detachably holds the filter 7. A membrane filter or the like is used as the filter 7. Sampled water passing through the filter 7 is guided to a flow meter 8 so that the flow rate thereof is measured. The result of the measurement by the flow meter 8 is provided to an operation circuit 9.

The operation and the method of use of the above-described embodiment is described hereinafter. First, a filter 7 is attached to the filter holder 6 for placement in filter housing 7. The filter housing 7 is then coupled to sampling pipe 2 by means of joints 5. Then, the manual valve 3 is opened to introduce sampled water from the water conduit 1. At this time, the pressure and the corresponding initial flow rate of the sampled water flowing through the sampling pipe 2 are determined by the constant pressure.maintaining valve 4.

Now, assuming that the initial flow rate passing through the filter 7 is $Q_0$ and the flow rate after a prescribed time is $Q_T$, then $Q_0 = Q_T$ if the filter 7 is not clogged. However, if the filter 7 is clogged with impurities contained in the sampled water, $Q_0 > Q_T$, and the ratio $Q_T/Q_0$ becomes smaller as more and more holes of the filter 7 are clogged. The operation circuit 9 evaluates the above-described flow rate ratio $Q_T/Q_0$ at a prescribed time interval. Therefore, the total amount or level of impurities in the sampled water can be measured indirectly by analyzing the result of operation of the operation circuit 9.

The result of operation of the operation circuit 9 may be plotted on a chart at the aforementioned prescribed time interval or it may be recorded on a recording medium such as a floppy disc, cassette tape or the like for subsequent data analysis by a computer, etc. Thus, the result of operation of the operation circuit 9 may be used in various ways.

The above-described apparatus for measuring impurities can be used repeatedly by replacing the filter 7, so that it is capable of continuous monitoring so that a sudden change in the quality of water can be detected.

By filtering sampled water for a long period of time (for example one to several tens of days), filter 7 is only gradually clogged, even if the characteristic particle diameter of the impurity is small, thereby enabling the measurement thereof. If a filter having a smaller characteristic hole diameter is used as the filter 7, it will be more effective. A preferred filter element pore size is one smaller than 0.1 $\mu$m.

In addition, due to the constant pressure valve 4, there will be no measurement error in the case of fluctuation of pressure and flow rate of the water flowing through the water conduit 1.

Although in the above embodiment, measurement of the total amount or level of impurities in flowing water was described, the present invention can be applied to the measurement of total amounts of impurities in chemicals provided that the filter used is chemical resistant.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An apparatus for continuously monitoring the level of filterable impurities in a flow of water comprising:

a sampling pipe having an outlet and an inlet in communication with a flow of water for continuously removing sample water from said flow;

means connected to said sampling pipe for maintaining a water pressure within said sampling pipe at a constant value;

filter means disposed at the outlet of said sampling pipe for filtering the sample water passing through said sampling pipe;

flow rate detecting means communicating with said apparatus downstream of said filter means for continuously detecting the flow rate of sample water passing through said filter means and generating a corresponding output as a function of time;

evaluating means coupled to said flow rate detecting means for determining ratios of the flow rate of the sample water passing through said filter means at predetermined times as compared to an initial flow rate of sample water passing through said filter means; and means for recording said ratios.

2. A device according to claim 1, wherein: said filter means comprises a filter element having pores smaller than 0.1 $\mu$m.

* * * * *